United States Patent

Chassot et al.

[11] Patent Number: 5,378,276
[45] Date of Patent: Jan. 3, 1995

[54] DIKETOPYRROLOPYRROLES CONTAINING NITROXYL GROUPS

[75] Inventors: Laurent Chassot, Praroman; Gary Wooden, Oberschrot, both of Switzerland

[73] Assignee: Ciba-Geigy Corporation, Ardsley, N.Y.

[21] Appl. No.: 198,016
[22] Filed: Feb. 17, 1994

[30] Foreign Application Priority Data

Feb. 23, 1993 [CH] Switzerland .................... 552/93

[51] Int. Cl.$^6$ ..................... C08K 5/34; C08K 5/32
[52] U.S. Cl. ..................... 106/493; 106/494; 106/498; 106/500; 106/505; 548/426
[58] Field of Search ............ 548/426; 106/493, 494, 106/498, 500, 505

[56] References Cited

U.S. PATENT DOCUMENTS

| | | | |
|---|---|---|---|
| 3,536,722 | 10/1970 | Murayama et al. | 546/20 |
| 3,936,456 | 2/1976 | Ramey et al. | 544/231 |
| 3,966,711 | 6/1976 | Rasberger | 540/492 |
| 3,970,632 | 7/1976 | Yoshiura et al. | 524/87 |
| 3,971,757 | 7/1976 | Rasberger | 524/106 |
| 4,131,599 | 12/1978 | Brunetti et al. | 524/102 |
| 4,415,685 | 11/1983 | Iqbal et al. | 524/92 |
| 4,866,113 | 9/1989 | Bitterli et al. | 524/87 |
| 4,920,228 | 4/1990 | Lai et al. | 546/224 |
| 4,921,962 | 5/1990 | Galbo et al. | 546/184 |
| 5,001,233 | 3/1991 | Murray et al. | 540/29 |
| 5,019,613 | 5/1991 | Ravichandran et al. | 524/100 |
| 5,021,483 | 6/1991 | Galbo | 524/100 |
| 5,021,486 | 6/1991 | Galbo | 524/100 |
| 5,021,577 | 6/1991 | Galbo | 546/188 |

FOREIGN PATENT DOCUMENTS

| | | |
|---|---|---|
| 0284800 | 10/1988 | European Pat. Off. |
| 309401 | 3/1989 | European Pat. Off. |
| 389428 | 9/1990 | European Pat. Off. |
| 2252372 | 11/1974 | France |
| 56-109635 | 1/1974 | Japan |
| 50-58141 | 5/1975 | Japan |
| 63-252758 | 10/1988 | Japan |

OTHER PUBLICATIONS

H. S. Freeman, et al, Dyes and Pigments vol. 17 (1991) pp. 83–100 no month.

Z. Ma et al. J. Org. Chem. vol. 56 (1991) pp. 6110–6114 no month.

T. Kurosaki et al, J. of Polymer Science vol. 12 pp. 1407–1420 (1974) no month.

R. W. Murray et al—Tetrahedron letters vol. 29, No. 37 pp. 4677–4680 (1988) no month.

J. B. Valodarsky, Imidazoline Netroxides vol. I, pp. 5–23, (1988) no month.

J. F. W. Keana. Chem. Reviews, vol. 78 (1978) No. 1 pp. 37–64 no month.

*Primary Examiner*—Karl Group
*Assistant Examiner*—Scott L. Hertzog
*Attorney, Agent, or Firm*—Michele A. Kovaleski

[57] ABSTRACT

Diketopyrrolopyrroles of formula

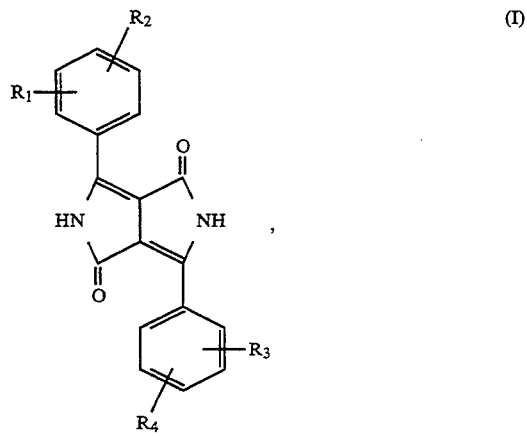

(I)

wherein $R_1$, $R_2$, $R_3$ and $R_4$ are each independently of one another hydrogen, chloro, $C_1$–$C_4$alkyl, methoxy, phenyl, cyano or a group $$-X_1-V-X_2-T-A,$$

in which at least one of $R_1$, $R_2$, $R_3$ or $R_4$ contains the group A,
A is a group of formula

11 Claims, No Drawings

DIKETOPYRROLOPYRROLES CONTAINING NITROXYL GROUPS

The present invention relates to diketopyrrolopyrroles containing nitroxyl or N-hydrocarbyloxyamino groups and to the use thereof as pigments or as light stabilisers for other diketopyrrolopyrroles.

Pyrrolo[3,4-c]pyrrole pigments have been known for some years and are disclosed, inter alia, in U.S. Pat. Nos. 4,415,685 and 4,579,949. A number have found acceptance as high-performance pigments. Although these pigments already have very good fastness to light and weathering, it has now surprisingly been found that these properties can be further enhanced without impairment of other properties, especially in the case of transparent pigment forms, by introducing a nitroxyl or N-hydrocarbyloxyamino group into the diketopyrrolopyrrole molecule or by blending a diketopyrrolopyrrole with a product that has been so modified.

Nitroxyl compounds are disclosed as stabilisers in different publications. JP-A 75-58141 discloses among many other HALS (hindered amine light stabilisers) nitroxyl compounds which, together with UV absorbers, are able to stabilise pigmented plastics against the action of light. It is claimed that the action of the UV absorbers as light stabilisers for the plastic material is impaired by the pigments, but that this impairment can be prevented by a HALS. Preferred HALS are those that do not contain a nitroxyl group. A polymer substance containing a quinophthalone pigment which, owing to the addition of a HALS, has superior fightfastness and fading resistance is disclosed in U.S. Pat. No. 3,970,632. Although nitroxyl compounds are generically embraced, mention is specifically made only of HALS that do not contain nitroxyl groups. JP-A 82-119941 discloses pigmented polymers containing a UV absorber and a HALS (making no reference to nitroxyl compounds) to prevent light-induced fading. JP-A 90-99323 discloses laminates stabilised against light-induced fading that contain in an interlayer a dye (incorrectly designated as pigment) that is soluble in an organic solvent and which has been treated in solution with a nitroxyl compound. Dyes and Pigments 17 (1991), 83-100, describes dyes containing built-in HALS residues with nitroxyl groups and U.S. Pat. No. 4,866,113 discloses nitroxyl-free organic pigments containing built-in HALS residues.

EP-A 309 401 teaches the use of N-hydroxy-HALS for preventing the embrittlement, cracking, corrosion, erosion, loss of gloss, chalking and yellowing of coatings containing specific organic pigments such as phthalocyanine and azo pigments.

N-Hydrocarbyloxy derivatives of HALS are disclosed, inter alia, in U.S. Pat. No. 4,921,962, U.S. Pat. Nos. 5,019,613, 5,021,483, 5,021,486, 5,021,577 and in EP-A 389 428 as light stabilisers for polymers. Attention is drawn in these references exclusively to the protective effect of these compounds against the light-induced degradation of high molecular weight organic material, typically polyolefins, elastomers, polyvinyl chloride, polyesters, polyurethanes, of coatings and enamels which are heat-curable at room temperature by acid catalysis.

The teaching to be inferred from the cited publications by those skilled in the art is that, when using soluble colourants which themselves contain a nitroxyl group or in which a nitroxyl group containing compound is incorporated, light-induced fading can be diminished, but that the same effect, when using pigments in which other properties such as dispersibility and resistance to heat and migration are important factors, is achieved by the presence of HALS that do not contain nitroxyl groups.

Surprisingly, novel diketopyrrolopyrroles containing nitroxyl or N-hydrocarbyloxyamino groups have now been found which, compared with conventional diketopyrrolopyrroles, have even better fastness to light and weathering without the impairment of other essential pigment properties.

Accordingly, the invention relates to diketopyrrolopyrroles of formula

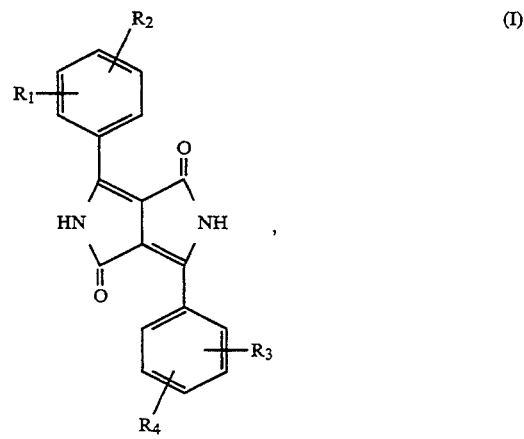

wherein $R_1$, $R_2$, $R_3$ and $R_4$ are each independently of one another hydrogen, chloro, $C_1$-$C_4$alkyl, methoxy, phenyl, cyano or a group $$-X_1-V-X_2-T-A,$$

in which at least one of $R_1$, $R_2$, $R_3$ or $R_4$ contains the group A, $X_1$ and $X_2$ are each independently of the other —O—, —S—, —N($R_5$)—, —CO— or —SO$_2$— or a direct bond, V is a group —(CH$_2$)$_m$—,

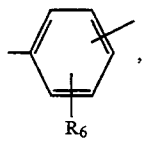

—(CH$_2$CH$_2$O))$_m$—CH$_2$CH$_2$— or a direct bond and m is 1 or 2, with the proviso that, if V is a direct bond, $X_1$ is also a direct bond, T is a group

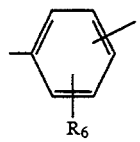

or —(CH$_2$)$_m$— and, if not linked to a nitrogen atom, may also be a direct bond, $R_5$ is hydrogen or $C_1$-$C_4$alkyl, and
$R_6$ is hydrogen, halogen or $C_1$-$C_4$alkyl,
A is a group of formula

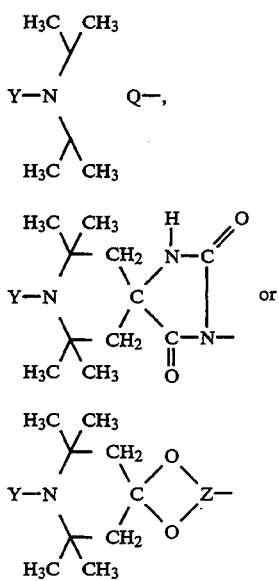
(II)

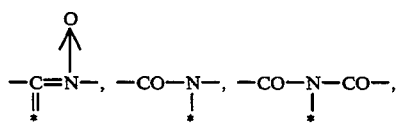
or (III)

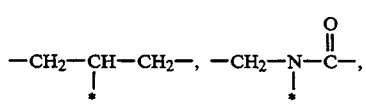
(IV)

wherein
Y is O., OH or OR, and R is $C_1$-$C_{12}$alkyl or $C_5C_{12}$cycloalkyl,
Q is a group of formula

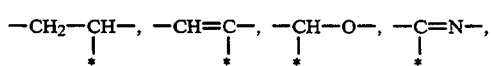

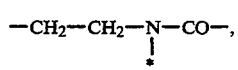

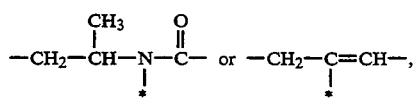

—$CH_2$—$CH_2$—N—CO—,

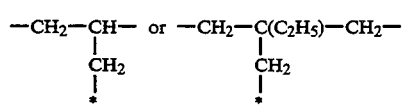

wherein the starred bond is the bond attached to T, and Z is a group of formula

—$CH_2$—CH— or —$CH_2$—C($C_2H_5$)—$CH_2$—
    |                        |
    $CH_2$                   $CH_2$
    *                        * wherein the starred bond is the bond attached to T.

Substituents defined as C1-C4alkyl are typically methyl, ethyl, n-propyl, isopropyl, n-butyl, sec-butyl or tert-butyl.

$R_7$ defined as halogen is typically bromo or, preferably, chloro.

R defined as $C_5$-$C_{12}$cycloalkyl is typically cyclopentyl, cycloheptyl, cyclodecyl or, preferably, cyclohexyl and, as $C_1$-$C_{12}$alkyl, is typically methyl, ethyl, n-propyl, isopropyl, n-butyl, sec-butyl, tert-butyl, n-amyl, tert-amyl, n-hexyl, n-heptyl, n-octyl, n-decyl or n-dodecyl.

Y is preferably OR, wherein R is tert-butyl, $C_7$-$C_{12}$alkyl or $C_5$-$C_6$cycloalkyl or, most preferably, O..

Unsymmetrical compounds of formula I, wherein only one of $R_3$ or $R_4$ is a group

are preferred.

Particularly interesting diketopyrrolopyrroles are those of formula

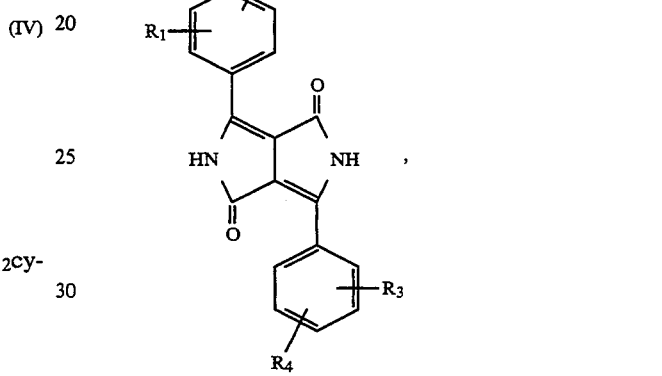
(V)

wherein $R_3$ is a group

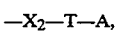

$R_1$, $R_2$ and $R_4$ are each independently of one another hydrogen, chloro, methyl, methoxy, cyano or phenyl, and $R_1$ may additionally be a group

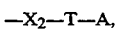

$X_2$ is —O— or —N($R_5$)—,
T is a group

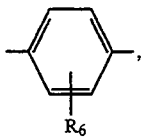

—($CH_2$)$_m$— or a direct bond,
$R_5$ and $R_6$ are hydrogen or methyl,
A is a group

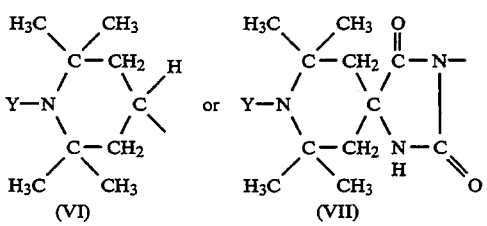

wherein

Y is O. or OR and R is tert-butyl, n-octyl or cyclohexyl.

Preferred diketopyrrolopyrroles are those of formula

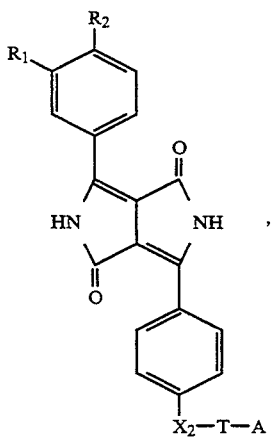 (VIII)

wherein one of $R_1$ and $R_2$ is hydrogen, chloro, methyl, phenyl or cyano and the other is hydrogen, $X_2$ is —O—.

T is a group

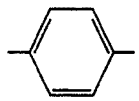

or a direct bond, and

A is a group of formula VI, wherein Y is O..

The diketopyrrolopyrroles of formula I can be prepared by known processes analogous to standard known ones, conveniently by reacting a disuccinate with a nitrile or a mixture of nitriles of formulae

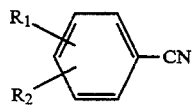 (IX)

and

 (X)

and as disclosed, inter alia, in U.S. Pat. No. 4,579,949 and U.S. Pat. No. 4,720,305, or, especially in the case of the preferred compounds of formula I, wherein only one of $R_3$ or $R_4$ is a group

—$X_1$—V—$X_2$—T—A, by reacting a pyrrolinone of formula

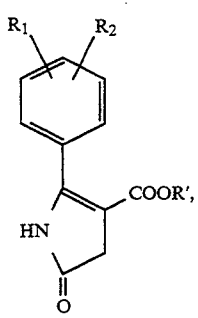 (XI)

or an enamine of formula

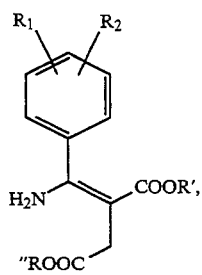 (XII)

with a nitrile of formula X, as taught, inter alia, in U.S. Pat. No. 4,659,775 and U.S. Pat. No. 4,749,795.

$R_1$, $R_2$, $R_3$ and $R_4$ in formulae IX, X, XI and XII have the meanings given above, with the proviso that at least one of these substituents and preferably one of $R_3$ and $R_4$ must be a group

—$X_1$—V—$X_2$—T—A as defined above.

R' and R" in formulae XI and XII are each independently of one another lower alkyl, typically methyl, ethyl, n-propyl, isopropyl, n-butyl, sec-butyl, tert-butyl and tert-amyl. Methyl and ethyl are preferred.

The compounds of formulae IX, X, XI and XII are known compounds. Any that are novel can be prepared by methods analogous to standard known ones. Nitriles of formulae IX and X, wherein at least one of $R_1$ and $R_2$ or of $R_3$ and $R_4$ is a group —$Y_1$—V—$X_2$—T—A, are either known or can be prepared by generally known methods, conveniently by reacting a nitrile of formula IX or X, wherein at least one of $R_1$ and $R_2$ or $R_3$ and $R_4$ is —$X_1$—V—$X_2$H, with a known compound of formula Cl—T—A.

To prepare nitriles in which —$X_1$—V—$X_2$—T—A is in para-position it is also possible to react para-chlorobenzonitrile with a compound of formula

H—$X_1$—V—$X_2$—T—A.

The diketopyrrolopyrroles of formula I are admirably suitable for use as pigments for colouring organic material of high molecular weight. They may also be used as stabilisers of conventional diketopyrrolopyrroles against the action of light and weathering that may result in fading and in some cases also in darkening of the colorations obtained with them.

Hence the invention also relates to pigment compositions comprising a) at least one diketopyrrolopyrrole of formula

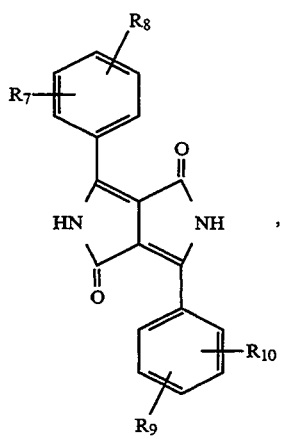

(XIII)

wherein $R_7$, $R_8$, $R_9$ and $R_{10}$ are each independently of the other hydrogen, chloro, $C_1$-$C_4$alkyl, methoxy, phenyl or cyano, and b) 0.1 to 20% by weight, based on the diketopyrrolopyrrole a), of a diketopyrrolopyrrole of formula I.

The novel pigment compositions are obtained by mixing both components a) and b).

The two components a) and b) are mixed by any of the commonly employed methods. Component b) can be admixed conveniently as moist press cake or as powder during the synthesis, the recrystallisation or the filtration of component a) with this latter. Components a) and b) can also be mixed by intensive mixing or milling, or they can be added to the high molecular weight organic material to be coloured and mixed during the dispersion process.

The diketopyrroles comprising component a) of the novel pigment compositions are known products and can be prepared conveniently in accordance with the processes described in U.S. Pat. No. 4,579,949 and U.S. Pat. No. 4,749,795.

The pigment compositions of this invention, like the novel diketopyrrolopyrroles are admirably suitable as pigments for colouring organic material of high molecular weight, especially whenever exacting demands are made of fastness to light and weathering.

Illustrative examples of organic materials of high molecular weight which can be coloured with the novel pigment compositions are cellulose ethers and esters, typically ethyl cellulose, nitrocellulose, cellulose acetate, cellulose butyrate, natural resins or synthetic resins, typically polymerisation or condensation resins such as aminoplasts, preferably urea/formaldehyde and melamine/formaldehyde resins, alkyd resins, phenolic plastics, polycarbonates, polyolefins, polystyrene, polyvinyl chloride, polyamides, polyurethanes, polyesters, ABS polymers, polyphenylene oxides, rubber, casein, silicone and silicone resins, singly or in mixtures.

The diketopyrrolopyrroles and pigment compositions of this invention are especially suitable for colouring polyvinyl chloride and polyolefins such as polyethylene and polypropylene as well as for pigmenting paint systems, coating materials and printing inks. Owing to their superior lightfastness they are also very suitable for use in electrophotographic materials (e.g. photocells), colour filters (e.g. liquid crystal displays), information storage materials (optical discs), non-linear optics and in optical limiters.

The preferred utility, however, of the diketopyrrolopyrroles and pigment compositions of this invention is for colouring aqueous and/or solvent-based paint systems, especially automotive lacquers. The most preferred utility is for effect finishes in which transparent organic pigments are used.

The above high molecular weight organic compounds may be singly or as mixtures in the form of plastics, melts or of spinning solutions, paint systems, coating materials or printing inks. Depending on the end use requirement, it is expedient to use the diketopyrrolopyrroles and pigment compositions of this invention as toners or in the form of preparations.

The diketopyrrolopyrroles and pigment compositions of this invention can be used in an amount of 0.01 to 40% by weight, preferably 0.1 to 20% by weight, based on the high molecular weight organic material to be pigmented.

The pigmenting of the high molecular weight organic materials with the diketopyrrolopyrroles and pigment compositions of this invention is conveniently effected by incorporating a said diketopyrrolopyrrole or pigment composition by itself or in the form of a masterbatch in the substrates using roll mills, mixing or milling apparatus. The pigmented material is then brought into the desired final form by methods which are known per se, conveniently by calendering, moulding, extruding, coating, spinning, casting or by injection moulding. It is often desirable to incorporate plasticisers into the high molecular weight compounds before processing in order to produce non-brittle mouldings or to diminish their brittleness. Suitable plasticisers are typically esters of phosphoric acid, phthalic acid or sebacic acid. The plasticisers may be incorporated before or after working the the diketopyrrolopyrrole or pigment composition of this invention into the polymers. To obtain different shades it is also possible to add fillers or other chromophoric components such as white, coloured or black pigments in any amount to the high molecular weight organic materials in addition to the diketopyrrolopyrrole or pigment composition of this invention.

For pigmenting paint systems, coating materials and printing inks, the high molecular weight organic materials and the diketopyrrolopyrroles and pigment compositions of this invention, together with optional additives such as fillers, other pigments, siccatives or plasticisers, are finely dispersed or dissolved in a common organic solvent or solvent mixture. The procedure may be such that the individual components by themselves, or also several jointly, are dispersed or dissolved in the solvent and thereafter all the components are mixed.

When used for colouring, inter alia, paint systems, polyvinyl chloride or polyolefins, the diketopyrrolopyrroles and pigment compositions of this invention have good allround pigment properties, such as good dispersibility, superior colour strength and purity, good fastness to migration and weathering, and, most especially, fastness to light and weathering.

The invention is illustrated by the following Examples in which, unless otherwise indicated, parts are by weight.

Example 1a)

A solution of 20.6 g of 4-chlorobenzonitrile and 25.8 g of an alcohol of formula

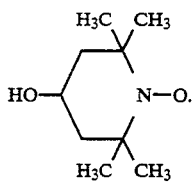

in 50 ml of N-methylpyrrolidone is added over 10 minutes to a stirred suspension of 4.3 g of sodium hydride in 20 ml of N-methylpyrrolidone. The resultant suspension is stirred for a further 16 hours at 95° C., and then 300 ml of ethyl acetate are added and the organic phase is extracted with water (3×100 ml) and dried over Na₂SO₄. The ethyl acetate is removed by distillation and the residue is dried under vacuum, giving 18.3 g of the nitrile of formula

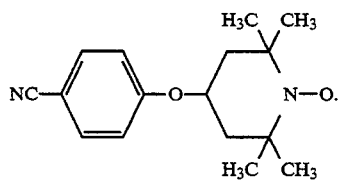

(XIV)

with a melting point of 141° C.

| Analysis: | C | H | N |
|---|---|---|---|
| calcd.: | 70.30% | 7.74% | 10.25% |
| found: | 70.35% | 7.85% | 10.12% | b); With vigorous stirring, 2.75 g of sodium are heated in 96 ml of tert-amyl alcohol at reflux until completely consumed. To the refluxing solution are first added 8.2 g of the nitrile of formula XIV obtained according to a) and then 8.28 g of the pyrrolinone of formula

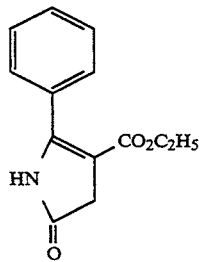

(XV)

in 4 increments over 1 hour. The resultant dark red mixture is refluxed for a further 2 hours, then cooled to room temperature and diluted with 100 ml of water. After adjusting the pH to 7 with acetic acid, the reaction mixture is filtered and the residue is washed first with methanol, then with water, and dried in a vacuum drying oven overnight at 90° C. to give 3.4 g of an orange-red pigment of formula

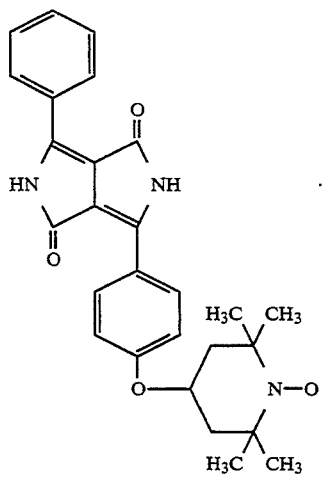

(XVI)

| Analysis: | C | H | N |
|---|---|---|---|
| calcd.: | 70.72 | 6.16 | 9.16 |
| found: | 70.16 | 6.50 | 8.68 |

Example 2

Example 1 is repeated, with the sole exception that the nitrile of formula XIV is replaced with an equivalent amount of a nitrile of formula

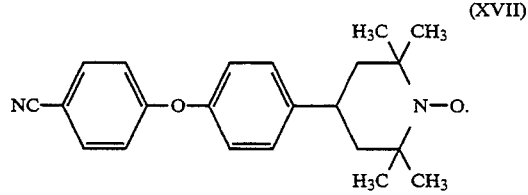

(XVII)

to give a pigment of formula

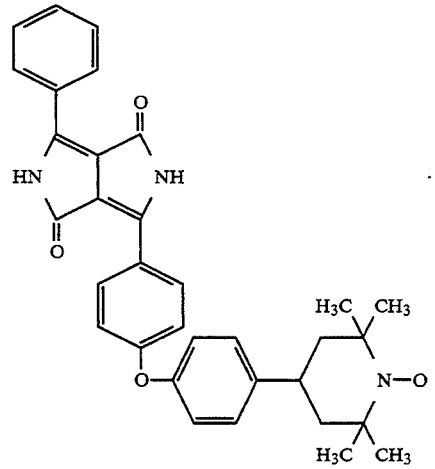

(XVIII)

Example 3

45.65 g of a moist press cake of the diketopyrrolopyrrole of formula

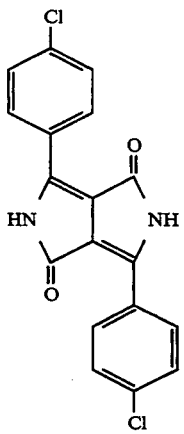

(XIX)

(21.9% solids content) are suspended in 200 ml of water by vigorously stirring for 30 minutes. A solution of 0.5 g of the product of Example 1 in 50 ml of N-methylpyrrolidone is added dropwise to the suspension over 20 minutes. The resultant suspension is heated for 1 hour to 50° C., then cooled to room temperature, filtered, washed with water and dried in a vacuum drying oven at 80° C., giving 11.56 g of a red pigment composition.

Example 4

Example 3 is repeated, but replacing the diketopyrrolopyrrole of formula XIX with the same amount by weight of the diketopyrrolopyrrole of formula (XX)

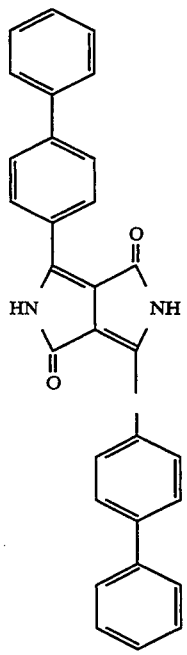

containing 2% by weight (based on XX) of the product of Example 1.

Example 5

Example 4 is repeated, with the sole exception that the product of Example 1 is replaced with the same amount by weight of the product of Example 2.

Example 6

The pigment obtained according to Example 1 is incorporated as follows in an alkyde/melamine storing varnish system:

0.4 g of pigment, 7.6 g of TiO₂, 9 ml of methyl isobutyl ketone and 30 g of a stoving varnish comprising 66.5 parts of alkyd resin ®ALKYDAL F27 (Bayer AG), 24.4 parts of melamine resin ®MAPRENAL TTK (Hoechst AG), 2.1 parts of xylene, 4.0 parts of ethylene glycol and 1.0 pan of silicone oil (1% in xylene) are mixed by conventional methods. The pigmented varnish so obtained is applied to sheet aluminium and stoved for 30 minutes at 130° C.

Further coloured coatings are prepared in exactly the same manner, with the sole exception that the product of Example 1 is replaced with the same amount by weight of each of the products of Examples 2, 3, 4 and 5.

Control coloured coatings are also pre pared in the same manner, but using conventional pigments of formulae

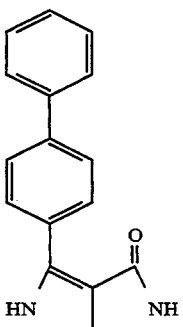

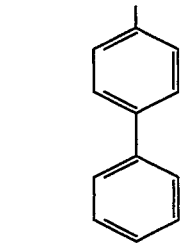

and

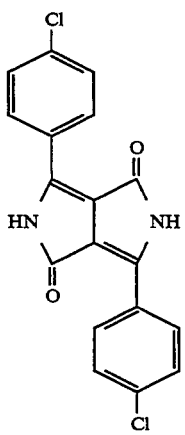

in place of the modified pigments of the invention.

The fastness to weathering of the coloured coatings is determined by the WOM Test according to DIN 53 387 after exposure to weathering for 500 hours. The fastness to weathering of all the coatings is found to be superior to that of the control finishes.

Example 7

22 g of the diketopyrrolopyrrole pigment of formula

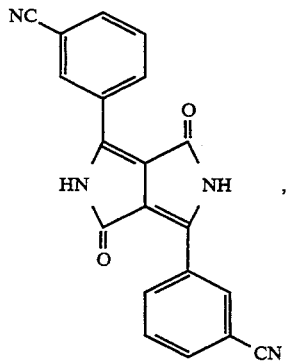

(XXI)

1.1 g of the pigments of formula XVI (Example 1) and 88 g of NaCl are charged to a laboratory kneader. Then 25 ml of N-methylpyrrolidone are added and the mixture is kneaded for 6 hours at 65° C. Afterwards the batch is charged into c. 1 l of water and stirred to a fine suspension for 3 hours with a toothed-disc stirrer. The suspension is filtered and the filter product is washed with water until salt-free and dried in a vacuum drying oven.

Example 8

| Formulation: | |
|---|---|
| Solution A | |
| 67.1 parts of A1: | 8.2% solution of 86 parts of cellulose acetobutyrate (25% in butyl acetate), 4 parts of zirconium octoate, 48 parts of SOLVESSO 150 ® (aromatic solvent ex ESSO), 70 parts of butyl acetate and 52 parts of xylene; |
| 24.8 parts of A2: | polyester resin DYNAPOL H 700 ® (60%, ex Dynamit Nobel); |
| 3.1 parts of A3: | melamine resin MAPRENAL MF 650 ® (55%, ex Hoechst AG). |
| Dispersion B | |
| 12.3 parts of | aluminium paste Silverline 3334 ® (Silverline); |
| 8.0 parts of | SOLVESSO 150 ®; |
| 59.34 parts of | A1; |
| 21.92 parts of | A2; |
| 2.74 parts of | A3. |

A 1:1 mixture of a) a dispersion obtained by conventional methods of 10 parts of a pigment mixture of Example 7 in solution A and b) of dispersion B is applied with a spray pistol.

After briefly drying in the air, a clear varnish based on a thermosetting acrylic varnish is applied and stoved at 130° C. for 30 minutes. An orange-red metal effect finish is obtained.

A control coloured coating, is prepared in the same manner, except that 10 parts of the pigment of formula XXI without addition of the pigment of formula XVI is used.

The fastness to weathering of the coloured coatings obtained is determined by the WOM Test after exposure to weathering for 2000 hours.

The fastness to weathering of the coloured coating containing the pigment of formula XVI is superior to that of the control coloured coating.

What is claimed is:

1. A diketopyrrolopyrrole of formula

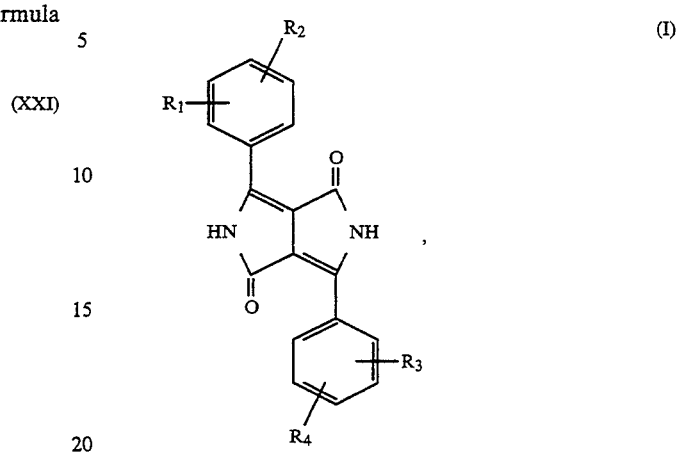

(I)

wherein $R_1$, $R_2$, $R_3$ and $R_4$ are each independently of one another hydrogen, chloro, $C_1$-$C_4$alkyl, methoxy, phenyl, cyano or a group

—$X_1$—V—$X_2$—T—A, in which at least one of $R_1$, $R_2$, $R_3$ or $R_4$ contains said group, $X_1$ and $X_2$ are each independently of the other —O—, —S—, —N($R_5$)—, —CO— or —$SO_2$— or a direct bond, V is a group —$(CH_2)_m$—,

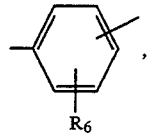

—$(CH_2CH_2O)_m$—$CH_2CH_2$— or a direct bond and m is 1 or 2, with the proviso that, if V is a direct bond, $X_1$ is also a direct bond, T is a group

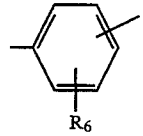

or —$(CH_2)_m$— and, if not linked to a nitrogen atom, may also be a direct bond, $R_5$ is hydrogen or $C_1$-$C_4$alkyl, and $R_6$ is hydrogen, halogen or $C_1$-$C_4$alkyl, A is a group of formula

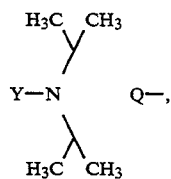

(II)

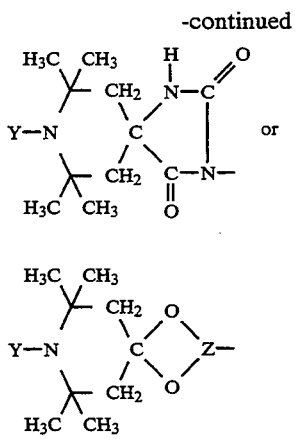 (III)

or

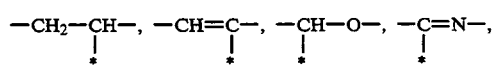 (IV)

wherein

Y is O., OH or OR, and R is $C_1$-$C_{12}$alkyl or $C_5$-$C_{12}$cycloalkyl,

Q is a group of formula

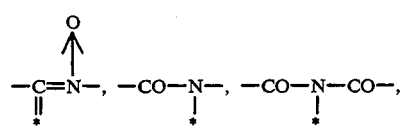

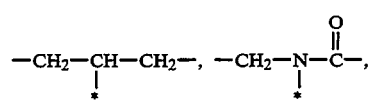

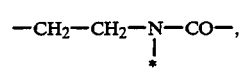

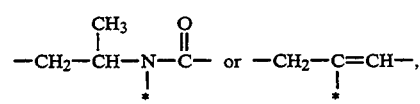

wherein the starred bond is the bond attached to T, and Z is a group of formula

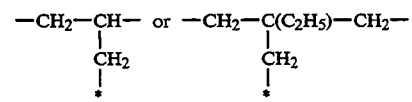

wherein the starred bond is the bond attached to T.

2. A diketopyrrolopyrrole according to claim 1 of formula I, wherein Y is O. or OR, and R is tert-butyl, $C_7$-$C_{12}$alkyl or $C_5$-$C_6$cyctoalkyl.

3. A diketopyrrolopyrrole according to claim 2 of formula

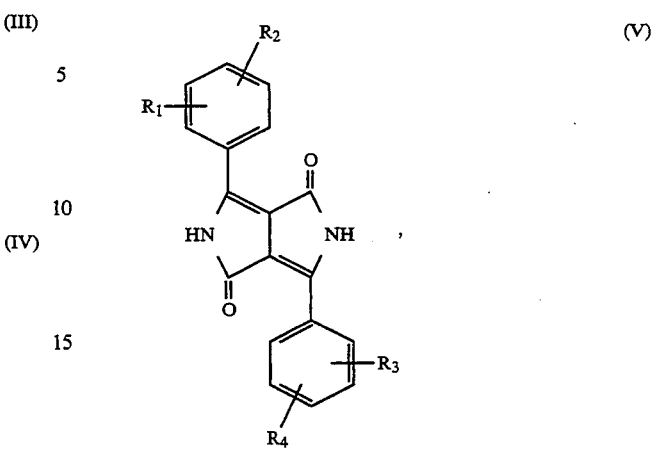 (V)

wherein $R_3$ is a group $$-X_2-T-A$$

$R_1$, $R_2$ and $R_4$ are each independently of one another hydrogen, chloro, methyl, methoxy, cyano or phenyl, and $R_l$ may additionally be a group $$-X_2-T-A,$$

$X_2$ is —O— or —N($R_5$)—,

T is a group

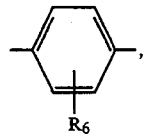

—($CH_2$)$_m$— or a direct bond, $R_5$ and $R_6$ are hydrogen or methyl,

A is a group

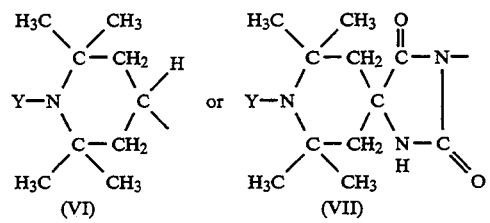

wherein

Y is O. or OR and R is tert-butyl, n-octyl or cyclohexyl.

4. A diketopyrrolopyrrole according to claim 3 of formula

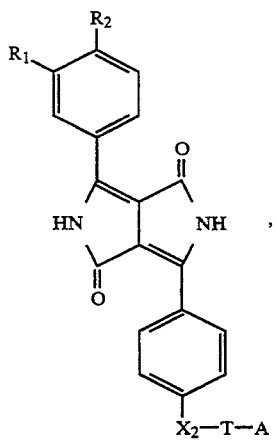

(VIII)

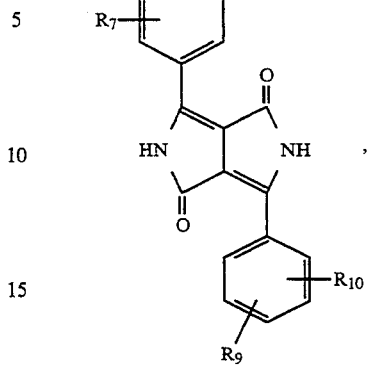

(XIII)

wherein one of $R_1$ and $R_2$ is hydrogen, chloro, methyl, phenyl or cyano and the other is hydrogen,
$X_2$ is —O—.
T is a group

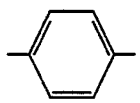

or a direct bond, and
A is a group of formula VI, wherein Y is O..

5. A pigment composition comprising
 a) at least one diketopyrrolopyrrole of formula wherein $R_7$, $R_8$, $R_9$ and $R_{10}$ are each independently of the other hydrogen, chloro, $C_1$-$C_4$alkyl, methoxy, phenyl or cyano, and
 b) 0.1 to 20% by weight, based on the diketopyrrolopyrrole a), of a diketopyrrolopyrrole of formula I as defined in claim 1.

6. High molecular weight organic material pigmented with a diketopyrrolopyrrole as claimed in claim 1.

7. High molecular weight organic material pigmented with a pigment composition as claimed in claim 5.

8. High molecular organic material as claimed in claim 6, which is a paint system.

9. A paint system as claimed in claim 8, which is an automotive lacquer.

10. High molecular organic material as claimed in claim 7, which is a paint system.

11. A paint system as claimed in claim 10, which is an automotive lacquer.

* * * * *